United States Patent [19]

Beplate

[11] Patent Number: 5,403,303
[45] Date of Patent: Apr. 4, 1995

[54] DIAPER CONSTRUCTION AND METHOD

[76] Inventor: Douglas K. Beplate, 10306 S. Ashley Park Dr., Sandy, Utah 84092

[21] Appl. No.: 80,416

[22] Filed: Jun. 18, 1993

Related U.S. Application Data

[60] Division of Ser. No. 845,629, Mar. 4, 1992, Pat. No. 5,221,277, which is a continuation-in-part of Ser. No. 650,927, Feb. 5, 1991, abandoned.

[51] Int. Cl.⁶ .................. A61F 13/15; A61F 13/20
[52] U.S. Cl. ............................ 604/394; 604/358; 604/378; 604/385.1; 604/393; 604/396; 604/402
[58] Field of Search ............... 604/358, 378, 385.1, 604/393, 394, 395, 396, 397, 398, 401, 402

[56] References Cited

U.S. PATENT DOCUMENTS

| | | | |
|---|---|---|---|
| 2,532,029 | 11/1950 | Medoff | 604/401 |
| 2,558,215 | 6/1951 | Habig et al. | 604/394 |
| 2,577,398 | 12/1951 | Blake | 604/394 |
| 2,691,983 | 10/1954 | Bernard | 604/401 |
| 2,893,393 | 7/1959 | Pressley | 604/394 |
| 3,489,149 | 1/1970 | Larson | 604/394 |
| 5,019,068 | 5/1991 | Perez et al. | 604/401 |

Primary Examiner—Randall L. Green
Assistant Examiner—P. Zuttarelli
Attorney, Agent, or Firm—J. Winslow Young

[57] ABSTRACT

A diaper configured with an inner panty enclosed within an outer panty, the inner panty having an absorbent pad inserted in an opening in the inner panty. The inner panty holds the absorbent pad snugly between the legs of the wearer but in spaced relationship to the outer panty. The outer panty is secured around its periphery to the inner panty and encloses both the absorbent pad and inner panty in spaced relationship. The spaced relationship forms an overflow reservoir beneath the absorbent pad.

2 Claims, 4 Drawing Sheets

DIAPER CONSTRUCTION AND METHOD

RELATED APPLICATIONS

This application is a divisional application of my application Ser. No. 07/845,629, filed 4 Mar. 1992, for DIAPER CONSTRUCTION AND METHOD and issued as U.S. Pat. No. 5,221,277, on 22 Jun. 1992, which application was a continuation-in-part of application Ser. No. 07/650,927, filed 5 Feb. 1991, for REUSABLE DIAPER AND METHOD, now abandoned.

BACKGROUND

1. Field of the Invention

This invention relates to diapers and, more particularly, to a novel, diaper and method whereby a pad of absorbent material is supported as an insert in a water-resistant inner shell, the inner shell being enclosed in a water-resistant, outer shell, the outer shell including a hook and loop fastener system along with elasticized leg openings.

2. The Prior Art

Diapers of one form or another have been known for many generations and are generally defined as a basic garment for human waste containment for infants and incontinent adults. A conventional diaper consists of a folded cloth or other absorbent material drawn up between the legs and fastened about the waist of the wearer. Historically, diapers were available in the form of a layer of cloth about one meter square. To produce a suitable diaper, the cloth was folded in any one of plurality of patterns to achieve the appropriate diaper size and then pinned with at least one safety pin to retain the diaper about the waist of the wearer. This entire process is fraught with problems not only in folding the diaper to the wrong size but also in injuries resulting from accidental punctures from the safety pin. Since the primary function of the diaper is to absorb urine and act as a catchment for feces, considerable effort has been made to reduce, or even eliminate, the natural revulsion one feels when required to change a diaper, particularly one containing feces. Cloth diapers also require the use of a separate, water-repellant cover to resist leakage of urine or even watery feces through the cloth fabric. The result of the foregoing is that within the past few decades there has been an explosive increase in the use of disposable diapers in both the pediatric and the adult settings. The primary driving force behind the wide acceptance of disposable diapers has been user convenience along with the aesthetics of easy disposability.

While convenient, disposable diapers represent not only a significant increase in cost but, more importantly, represent a major concern environmentally in that they constitute a significant portion of the solid waste stream. This, in turn, means that a significant portion of the landfill space is occupied by disposable diapers. Further, since a significant number of the disposable diapers contain feces, they also represent a threat to the environment through fecal contamination particularly due to the pathogens carried in most feces. One of the principal advantages to the use of cloth or reusable diapers is the fact that the human wastes are directed into the sewer system. However, a disposable diaper that uses less material in its construction without any corresponding decrease in its functionality will also prove to constitute a significant advancement in the art.

Numerous undergarments are known in the art and include, for example, a disposable combination panty and sanitary napkin as shown by Titone et al (U.S. Pat. No. 2,748,772). The panty portion includes a pocket-like crotch portion into which a sanitary napkin is enclosed during manufacture of the panty.

Blaufus (U.S. Pat. No. 2,754,824) discloses a diaper garment constructed from a sheet of moisture repellant material and having a pair of longitudinal pockets along each side and spaced an incremental distance apart. An absorbent pad is held in the pockets and receives waste deposited thereon.

Parravicini (U.S. Pat. No. 3,424,162) discloses an hygienic panty designed to be thrown away after use. Advantageously, a conventional cellulose material is used for the body portion of the panty while an insert of cotton gauze is used in the crotch portion of the panty.

Rickard (U.S. Pat. No. 3,599,638) discloses a disposable panty having a crotch construction adapted to receive a sanitary napkin, the sanitary napkin being replaceable without disposing of the panty so that the same panty can be used with several sanitary napkins.

De Woskin (U.S. Pat. No. 3,613,686) discloses a panty having a special crotch section adapted to hold a sanitary napkin snugly in place without fasteners or other attachments.

Tong (U.S. Pat. No. 352,356) discloses a urinary incontinence garment constructed with a panty-like configuration. A pouch inside the panty is adapted to receive an absorbent pad.

Davis (U.S. Pat. No. 4,568,342) discloses a variable-size, reusable diaper that utilizes a hook and loop fastener system to readily adapt the diaper to different wearer sizes.

Steer (U.S. Pat. No. 4,695,279) discloses a pair of incontinence briefs having a pocket located in the crotch region. An absorbent pad is removably inserted into the pocket.

Proxmire et al U.S. Pat. No. 4,770,656 discloses a disposable diaper having leg and waist gathers for form-fitting, self-adjusting disposable diapers.

Khan (U.S. Pat. No. 4,834,737) discloses a disposable diaper having a liquid impervious back sheet to which the absorbent padding is attached.

Cottenden (U.S. Pat. No. 4,898,594) discloses an incontinence garment having an absorbent pad sewn into the garment. The absorbent pad is enclosed in a liquid-impervious material and secured thereto by stitching that is carefully designed to preclude the capillary flow of urine along the stitching.

Van Gompel et al (U.S. Pat. No. 4,938,757 and 4,940,464) discloses a disposable pant-like garment having a liquid pervious liner, a liquid impervious outer cover and an absorbent medium between the liner and the cover.

Mc Cloud (U.S. Pat. No. 4,961,736) discloses a reusable cloth diaper having a highly absorbent inner liner permanently attached at one edge to an absorbent panel.

Clearly, each prior art diaper and/or sanitary garment has its advantages and disadvantages. Accordingly, it would be a significant advancement in the art to provide a diaper and method that incorporates selected advantages from each system. It would also be an advancement in the art to provide a diaper that includes an absorbent pad suspended in an inner shell and enclosed within a water-resistant outer shell. Another advancement would be to provide a diaper having a removable liner to facilitate transfer of feces from the diaper to the toilet or other waste disposal facility. Such a novel diaper and method is disclosed and claimed herein.

BRIEF SUMMARY AND OBJECTS OF THE INVENTION

This invention relates to a diaper configured with an absorbent, cloth-covered pad incorporated as an integral unit in an inner shell, the inner shell being enclosed in an outer, water-resistant shell. The inner shell suspends the absorbent pad snugly between the legs of the wearer and in spaced relationship to the outer shell. The inner shell in the region of the absorbent pad is in fluid communication with the spacial separation between the inner shell and the outer shell to allow surplus liquid to pass into this space. The inner shell also supports the absorbent pad in the extended configuration to resist its bunching during periods of wear. An optional liner is available to facilitate removal of any feces deposited in the diaper. The liner can be either reusable or disposable. A hook and hoop fastener system fastens the diaper about the waist of the wearer. Elasticized sections at each side of the diaper provide a snug fit around the legs of the wearer.

It is, therefore, a primary object of this invention to provide improvements in diapers.

Another object of this invention is to provide a diaper characterized by the absence of absorbent material on the external profile of the legs of the wearer.

Another object of this invention is to provide improvements in the method of providing a diaper.

Another object of this invention is to provide a diaper having an absorbent pad incorporated into an inner shell with the inner shell enclosed in a water-resistant, outer shell.

Another object of this invention is to provide a diaper having a removable liner to facilitate removal and disposal of feces collected in the diaper.

Another object of this invention is to provide a diaper having an absorbent pad supported snugly between the legs of a wearer, the absorbent pad being held against twisting or bunching while being held snugly between the legs of the wearer.

Another object of this invention is to provide a diaper having a hook and loop fastener system for adjustably fastening the diaper about the waist of the wearer.

These and other objects and features of this invention will become more readily apparent from the following description, the accompanying drawing and the appended claims.

DETAILED DESCRIPTION OF THE PREFERRED EMBODIMENT

The invention is best understood from the following description with reference to the accompanying drawing wherein like parts are designated by like numerals throughout.

General Discussion

Diapers are important not only for the pediatric population but also for certain segments of the adult population. The term "diaper" is used herein in a generic sense for any absorbent-type undergarment worn for the catchment and containment of urine and/or feces. The need for diapers among the pediatric population is accepted knowledge and is due to the fact that in practically all cases of pediatric diaper usage, the diaper is a temporary (up to three or four years) measure until the wearer's physiological maturity progresses sufficiently to the point where the normal excretory functions can be controlled voluntarily. The term "pediatric population" is usually understood to mean those persons up to about three or four years of chronological age and a weight up to about 40 pounds (18 kilograms). The term "adult population" is used herein to describe all other persons who may require the use of a diaper either in an acute sense or a chronic sense.

Usage of diapers by the adult population is generally the result of enuresis, injury, mental and/or physical deterioration, disease, confinement, incontinence, and the like, regardless of the origin of the particular problem. For instance, many women suffer from certain forms of urinary incontinence due to injuries inflicted on the bladder sphincter during childbirth. Physical incapacity as well as mental dementia, particularly among the geriatric portion of the adult population, appears to be the major factor necessitating the use of diapers among this population. In either circumstance, it is important for the wearer that the diaper should be easily donned either by the wearer or another person and changeable with equal facility.

Advantageously, the novel diaper of this invention is configured with an absorbent pad that is held snugly in place between the legs and is particularly characterized by the absence of padding on the outside of the profile of the legs. This means that, unlike many prior art diapers, there is no extraneous bulk around the waist or legs of the wearer to reveal to the casual observer that the wearer is wearing a diaper. Not only does this feature enable the ambulatory wearer to wear the diaper of this invention under normal clothing but it also significantly enhances the self esteem of the wearer by the knowledge that the presence of a diaper on the wearer is effectively hidden from accidental discovery or observation. The novel diaper system of this invention is either reusable or disposable. The reduced bulk of this diaper means that it will occupy less space in the waste disposal system.

Detailed Description

Figure 1:
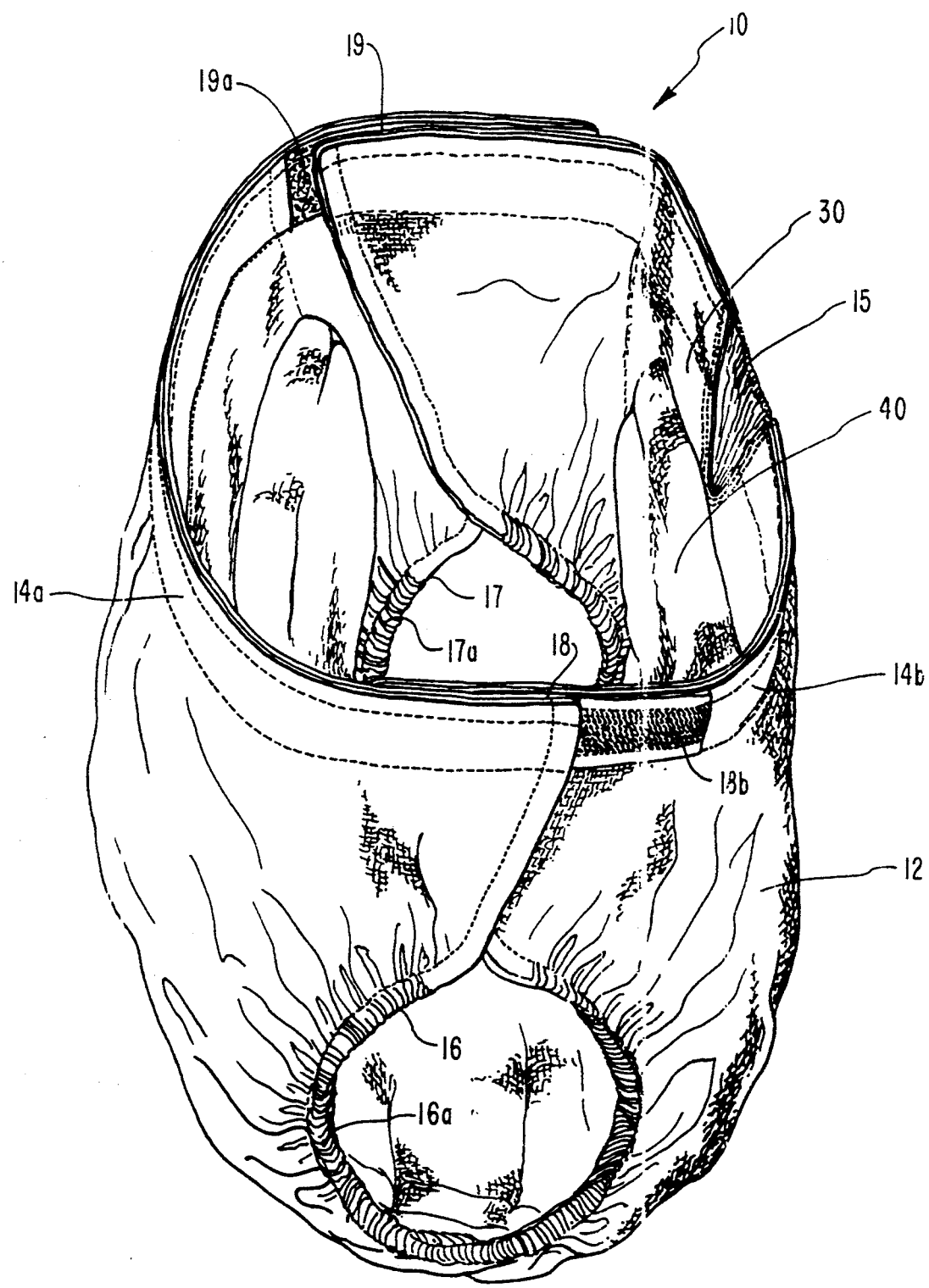
FIG. 1 is a perspective view of the novel diaper of this invention.

Referring now more particularly to FIG. 1, the novel, diaper of this invention is shown generally at 10 and includes an outer panty or outer shell 12 and an inner panty or inner shell 30 with inner shell 30 supporting an absorbent pad 40 in spaced relationship inside outer shell 12. Diaper 10 is configured with a panty-like external profile having leg openings 16 and 17 along with a waist band 14 separated into a front waist band 14a and a rear waist band 14b. Front waist band 14a is configured to be releasably joined to rear waist band 14b at each side of diaper 10 above leg openings 16 and 17. Leg opening 16 is designed as an opening for the left leg of a wearer (not shown) and includes an elasticized segment 16a to assure a snug fit about the leg (not shown) while leg opening 17 is correspondingly configured with an elasticized segment 17a to accommodate the right leg of the wearer (not shown) in a snug-fitting relationship.

The releasable joinder of the ends of front waist band 14a to the respective ends of rear waist band 14b is accomplished using matching pairs of hook and loop fastener systems 18 and 19. Loop portions 18a and 19a of hook and loop fastener systems 18 and 19, respectively, are attached at each end of front waist band 14a while hook portion 18b and hook portion 19b (FIG. 4) are attached at each end and on the outside face of rear waist band 14b. This particular orientation of the respective hook and loop portions of hook and loop fasteners 18 and 19 is important due to the inherent nature of commercially available hook and loop fastener systems. In particular, the loop portion is generally configured with a relatively soft, felt-like texture whereas the hook portion is specifically designed with a certain degree of stiffness to enable the hooks therein to suitably penetrate the loops so as to releasably engage the same. Such hook and loop fastener systems are widely available commercially from Velcro, Inc., Manchester, N.H., under their trademark VELCRO. In view of the relatively soft, felt-like texture of loop portions 18a (FIGS. 2-4) and 19a, they are placed on the inner face of front waist band 14a where any exposed portions thereof (as shown in FIG. 1 by loop portion 19a) are placed in contact with the wearer (not shown). It is particularly important that hook portions 18b and 19b (FIG. 4) are placed on the outside face of rear waist band 14b so as to minimize contact by the wearer (not shown).

At this point of the description of the various features included in diaper 10, it should be pointed out that even though diaper 10 can be fully reusable, the same, novel features can be incorporated, advantageously, into a diaper 10 that is entirely disposable. As such, diaper 10 provides significant advantages in that the total bulk thereof as the result of the overall size and placement of absorbent pad 40 is substantially reduced as compared to a commercially available, disposable diaper (not shown). In particular, absorbent pad 40 as well as inner shell 30 and outer shell 14 can be fabricated entirely from materials acceptable as solid wastes and, as such, provide significant advantages since the overall bulk of absorbent pad 40 is substantially less than the conventional, commercially available, disposable diaper (not shown).

An elastic gore 15 of an elastic fabric is inserted in the center of rear waist band 14b. Elastic gore 15 is designed to enhance the fit of waist band 14 about the waist of a wearer (not shown) by providing a limited degree of elasticity to waist band 14. This amount of elasticity is sufficient to adapt waist band 14 to changes to the circumference of waist of the wearer (not shown) during movement, changes in posture, breathing, and the like.

Figure 2:
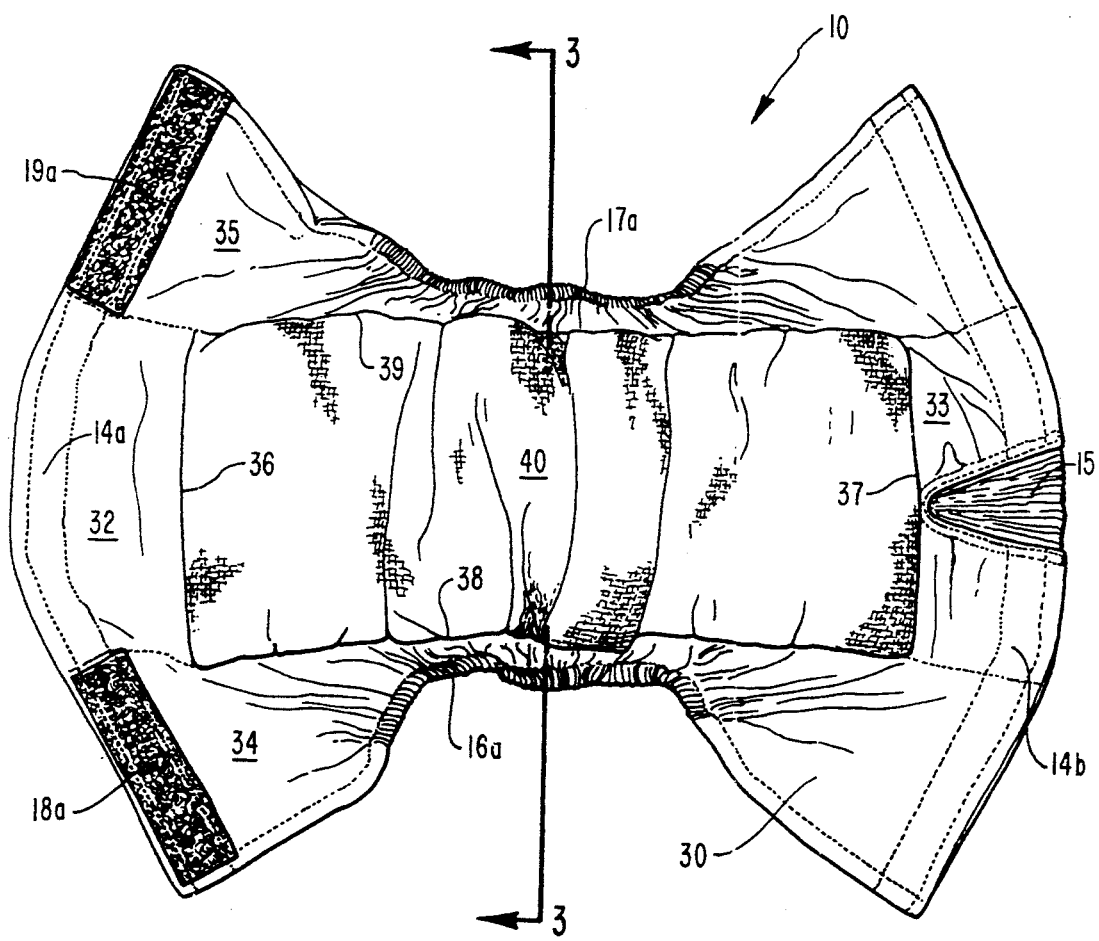
FIG. 2 is a plan view of the novel diaper shown in FIG. 1 but with the diaper opened.

Referring now also to FIG. 2, inner shell 30 generally conforms to the external profile of outer shell 12 but is assembled from a front panel 32, a rear panel 33, a left panel 34, and a right panel 35. Front panel 32 is joined to a front end of absorbent pad 40 along a seam 36 while rear panel 33 is joined to a rear end of absorbent pad 40 along a seam 37. Left panel 34 extends the full length of inner shell 30 and is joined along a seam 38 to a left edge of each of front panel 32, absorbent pad 40, and rear panel 33. Similarly, right panel 35 extends the full length of inner shell 30 and is joined along a seam 39 to the right side of each of front panel 32, absorbent pad 40, and rear panel 33.

Figure 3:
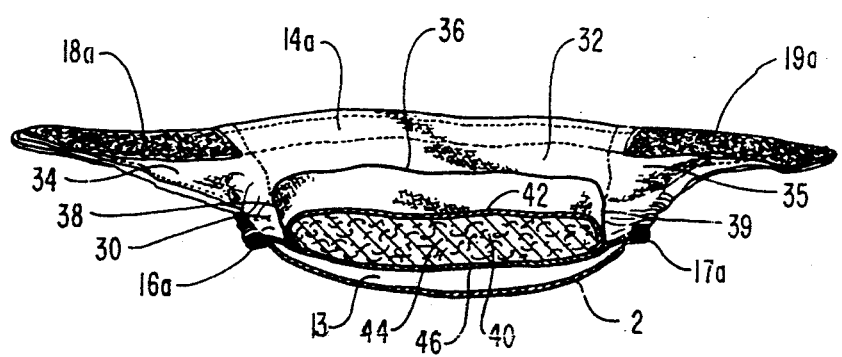
FIG. 3 is a cross sectional view taken along lines 3—3 of FIG. 2.

Inner shell 30 is designed to suspend absorbent pad 40 in spaced relationship between leg openings 16 and 17 (FIG. 1) and thereby suspend absorbent pad 40 snugly between the legs of the wearer (not shown) when waist band 14 is snugly engaged around the waist of the same. Further, inner shell 30 is also specifically configured to suspend absorbent pad 40 in spaced relationship within the profile of outer shell 12. With particular reference also to FIG. 3, absorbent pad 40 is shown in this cross sectional view as being suspended by inner shell 30 in spaced relationship to outer shell 12, the spatial separation therebetween being shown as spatial separation 13.

Absorbent pad 40 is configured from an upper layer 42 and a lower layer 46 with a fiber fill 44 therebetween. Upper layer 42 and lower layer 46 are fabricated from a soft fabric material such as a cotton flannel while fiber fill 44 is selected from a nonwoven, batting-type material such as a polyester, or the like. In one presently preferred embodiment fiber fill 44 is selected from a blended cotton and wool batting. In effect, absorbent pad 40 is constructed as a small quilt or pillow whose primary function is the absorption and retention of liquids. Upper layer 42 is specifically directed to a soft, absorbent, nonallergenic material such as cotton flannel, since its primary function is to reside snugly between the legs of a wearer and wick away any moisture deposited thereon. The moisture (not shown) is pulled directly into fiber fill 44 through this inherent wick action.

Spatial separation 13 allows outer shell 12 to assume a loose, slightly bouffant profile when secured to a wearer with the additional advantage of forming an overflow reservoir in the event excess liquid is deposited in absorbent pad 40. However, given the nature of absorbent pad 40 this eventuality is somewhat limited. For example, in one experimental test, over 280 milliliters of water were poured on and absorbed by absorbent pad 40 without any of the water passing into spatial separation 13. This particular experiment was conducted using a pediatric size, diaper 10. The advantage of absorbent pad 40 in such a circumstance is more clearly understood when it is pointed out that a pediatric wearer (not shown) of diaper 10 has normal bladder capacity of only about 85 milliliters.

Absorbent pad 40 performs another unique function when reusable diaper 10 is used in an adult setting. In particular, for those instances of bladder incontinence, the outflow of urine is more or less a constant drip generally at a rate that approximates the excretion of urine from the kidneys. In such circumstances, it is highly desirable for upper layer 42 to wick away this liquid directly into fiber fill 44. Absorbent pad 40 thereby quickly and efficiently retains the absorbed liquid while inner shell 30 suspends absorbent pad between leg openings 16 and 17. This feature is important since it effectively inhibits excess liquid in absorbent pad 40 from leaking out of either of leg openings 16 or 17.

Outer shell 12 and inner shell 30 are each fabricated from a water resistant fabric such as a nylon. This feature is important not only with respect to outer shell 12 and the fact that it creates an overflow reservoir in spatial separation 13, but also because it also effectively inhibits the migration or wick action of liquid from absorbent pad 40 through either of left panel 34 or right panel 35 to the respective leg openings, leg opening 16 or leg opening 17.

Figure 4:
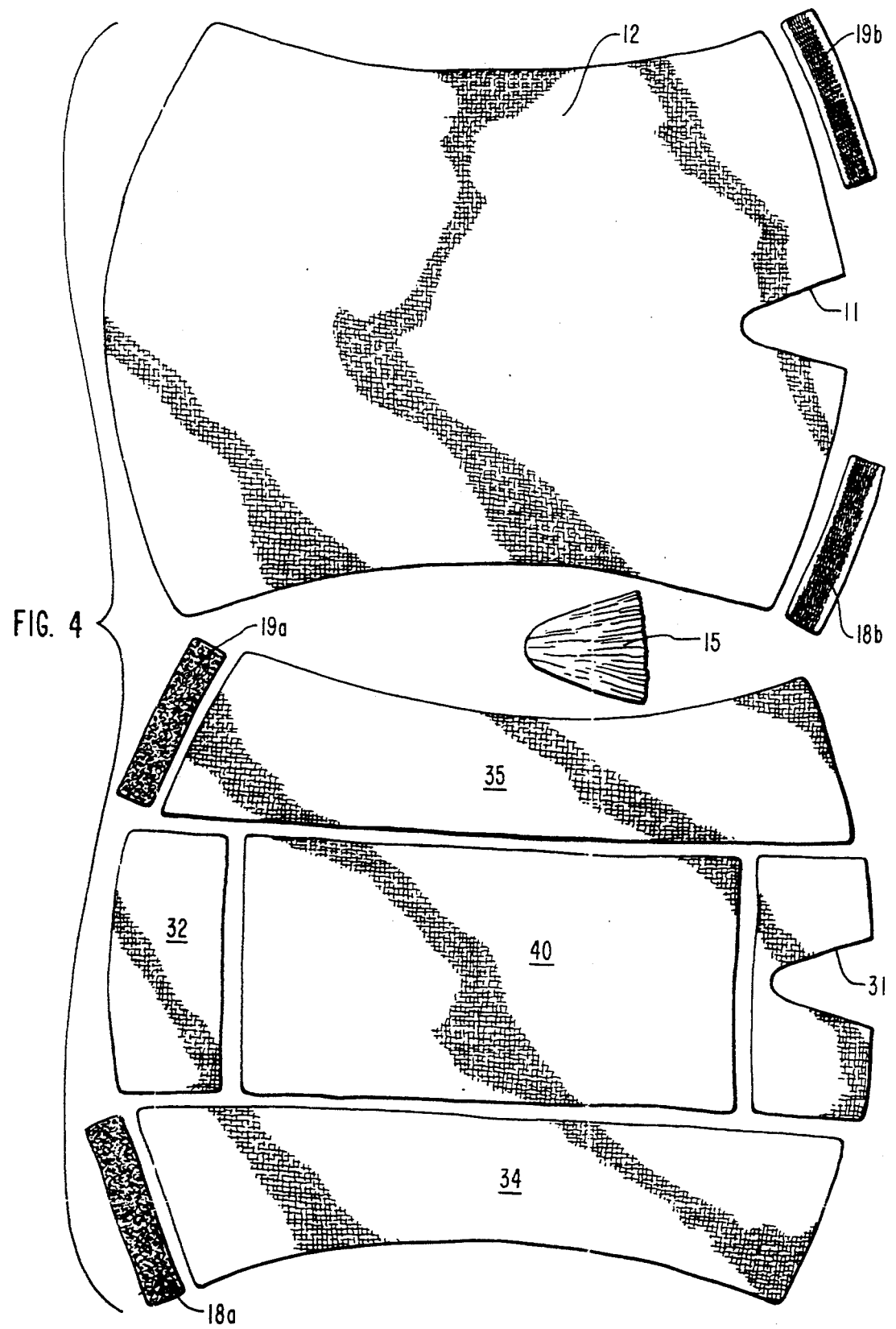
FIG. 4 is an exploded plan view of the various elements that are assembled into the diaper shown in FIG. 1.

With reference now to FIG. 4, outer shell 12 and inner shell 30 are shown in an exploded plan view of the various elements that are assembled to create diaper 10. Outer shell 12 includes a cutout 11 adapted to receive elastic gore 15. A matching cutout 31 is also found in rear panel 33 and, when superimposed over cutout 11 conforms to the profile of elastic gore 15.

Figure 5:
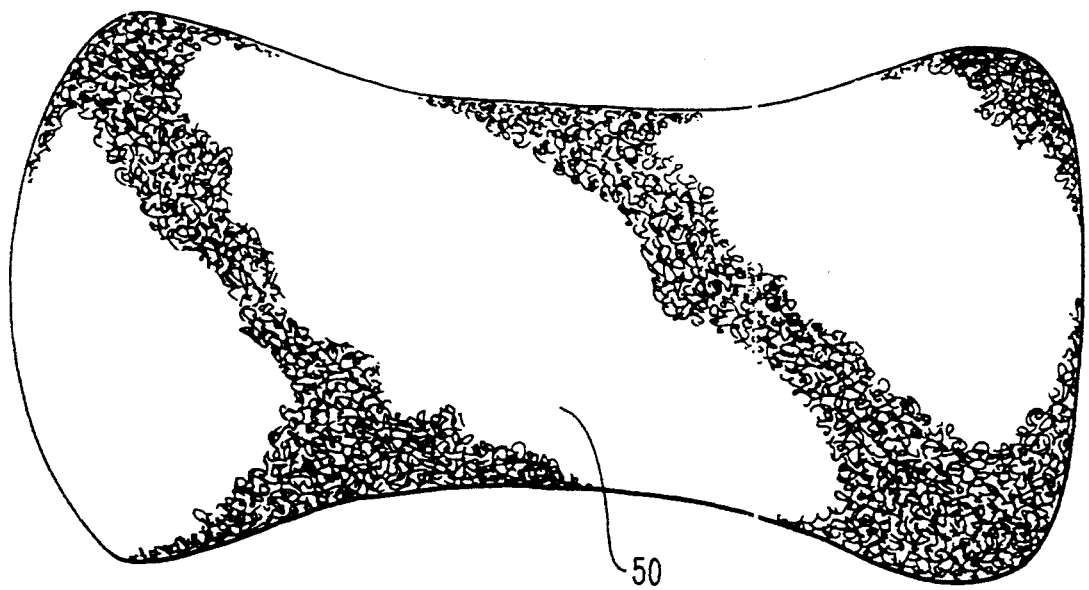
FIG. 5 is a plan view of the removable liner for the novel reusable diaper of this invention.

FIG. 5 shows a liner 50 that is adapted to be placed on top of absorbent pad 40 for the purpose of acting as a catchment for the solids part of feces excreted by the wearer (not shown) of diaper 10. Liner 50 may be fabricated from a flannel cloth material with the intention of being either reusable or even disposable. As a reusable item, liner 50 significantly reduces handling problems when feces (not shown) is deposited thereon since it is a simple matter for the attendant (not shown) to simply grasp each end of liner 50 and transport it to the appropriate waste receptacle (not shown). As a disposable system, liner 50 is fabricated from a suitable fabric material commonly found in disposable diapers, for example, and deposited directly into a toilet for disposal.

The Method

Diaper 10 is assembled with inner shell 30 enclosed within outer shell 12. Absorbent pad 40 is suspended in inner shell 30 and is specially configured to be held snugly between the legs of the wearer (not shown). Inner shell 30 is configured with a modified hour glass-like outline as is outer shell 12 so as to readily adapt diaper 10 to being worn between the legs of the wearer (not shown). Inner shell 30 is joined to outer shell 12 along their respective external perimeters so as to effectively enclose absorbent pad 40 inside the confines of outer shell 12. Importantly, absorbent pad 40 is not merely attached to an upper surface of inner shell 12 but is, in effect, inserted in an opening formed therein through the joinder of front panel 32 and rear panel 33 with each of left panel 34 and right panel 35. In this manner, excess liquid (not shown) received by absorbent pad 40 is free to enter spatial separation 13 thereby significantly reducing the possibility that the excess liquid could escape from either of leg openings 16 and 17. Clearly, if absorbent pad 40 were placed directly on top of a water-resistant fabric (such as if inner shell 30 were constructed similarly to outer shell 12) there would be a very high probability that the excess liquid would leak out of either of leg openings 16 and 17.

Diaper 10 is readily mounted and removed from about the waist of the wearer (not shown). Mounting is accomplished by bringing absorbent pad 40 snugly between the legs and fastening waist band 14 about the waist. Hook and loop fasteners 18 and 19 each have sufficient length to accommodate adjustably securing waist band 14. Further, elastic gore 15 contributes a limited degree of elasticity to waist band 14 to accommodate changes in the circumference of waist band 14 during wear of diaper 10.

Advantageously, since all of the bulk of absorbent pad 40 is held between the legs, the only visible portion of diaper 10 on the outsides of the legs are the respective portions of inner shell 30 and outer shell 12. Accordingly, excessive bulk is utterly eliminated from those portions of diaper 10 which would otherwise create an unsightly bulge in the outer clothing of the wearer. This is important particularly when diaper 10 is configured as an undergarment for a member of the adult population.

Diaper 10 is easily replaced by simply separating hook and loop fasteners 18 and 19 and removing absorbent pad 40 from between the legs of the wearer. Since the total bulk of diaper 10 is substantially smaller than that of a conventional disposable diaper as well as a conventional reusable diaper, diaper 10 is readily concealable (if necessary) for transportation to a place for washing the same.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for providing a diaper for a person comprising:

obtaining an absorbent pad to be worn between the legs of said person, said absorbent pad having an external profile with a first set of dimensions and including an upper fabric layer, a lower fabric layer, and a fibrous fill between said upper fabric layer and said lower fabric layer;

shaping an inner shell to be worn as an inner panty by said wearer, said inner shell being fabricated from a liquid resistant fabric and having a first, external periphery, said inner shell having an elongated aperture, said elongated aperture having an internal periphery with a second set of dimensions, said second set of dimensions of said elongated aperture corresponding to said first set of dimensions of said absorbent pad;

mounting said absorbent pad in said elongated aperture in said inner shell;

cutting an outer shell from said liquid resistant fabric, said outer shell forming an outer panty having a second, external periphery;

joining said inner panty to said outer panty along said first, external periphery and said second, external periphery thereby enclosing said inner shell in said outer shell;

forming a surplus liquid reservoir below said absorbent pad by holding said outer panty in spaced relationship away from said inner panty and said absorbent pad; and attaching said inner panty and said outer panty about the waist of the person, said inner panty supporting said absorbent pad snugly between the legs of the person.

2. The method defined in claim 1 wherein said preparing step includes limiting said first set of dimensions of said external periphery of said absorbent pad so as to preclude said absorbent pad from extending outwardly to the sides of said inner panty into contract with the legs.

* * * * *